United States Patent [19]

Nashef et al.

[11] Patent Number: 4,674,488
[45] Date of Patent: Jun. 23, 1987

[54] METHOD OF TREATING BONE FRACTURES TO REDUCE FORMATION OF FIBROUS ADHESIONS

[75] Inventors: Aws S. Nashef, Costa Mesa; Todd D. Campbell, Corona, both of Calif.

[73] Assignee: American Hospital Supply Corporation, Deerfield, Ill.

[21] Appl. No.: 707,954

[22] Filed: Mar. 4, 1985

[51] Int. Cl.⁴ .............................................. A61F 5/04
[52] U.S. Cl. .............................. 128/92 W; 128/92 YJ
[58] Field of Search ............ 128/92 G, 92 W, 92 VJ, 128/92 YD, 92 R

[56] References Cited
U.S. PATENT DOCUMENTS

| 3,710,789 | 1/1973 | Ersek | 128/92 G |
| 3,988,782 | 11/1976 | Dardik et al. | 3/1 |
| 4,158,893 | 6/1979 | Swanson | 3/1.91 |
| 4,186,448 | 2/1980 | Brekke | 128/92 G |
| 4,218,782 | 8/1980 | Rygg | 3/1.5 |
| 4,378,224 | 3/1983 | Nimni et al. | 8/94.11 |
| 4,400,833 | 8/1983 | Kurland | 3/1 |
| 4,430,760 | 2/1984 | Smestad | 128/92 G |
| 4,472,840 | 9/1984 | Jefferies | 128/92 G |
| 4,516,276 | 5/1985 | Mittelmeier et al. | 128/92 G |

Primary Examiner—C. Fred Rosenbaum
Assistant Examiner—C. W. Shedd
Attorney, Agent, or Firm—Bernard, Rothwell & Brown

[57] ABSTRACT

A method of treating a bone fracture which involves interposing a barrier layer of soft biological tissue at the interface of the bone and surrounding tissue.

9 Claims, 1 Drawing Figure

METHOD OF TREATING BONE FRACTURES TO REDUCE FORMATION OF FIBROUS ADHESIONS

BACKGROUND OF THE INVENTION

The present invention relates to a method of treating a bone fracture. More particularly the invention concerns a method of treating a bone fracture to minimize the formation of fibrous adhesions between the healing bone and adjacent surrounding tissue.

Injury to tendons and bones as a result of crushing or lacerating trauma requires special therapy following the preliminary wound healing. Typically, surgical repair of damaged tendons and fractured bones is followed by immobilization of the repair site for a period of 4-6 weeks. A problem associated with the healing process following setting of a bone fracture often arises at the interface of the growing bone and the adjacent tendons, muscles, nerves, and other surrounding tissues. Sharp, jagged, irregular bone edges ordinarily forms in the area of the fracture during the healing process. Bony spurs promote the growth of fibrous adhesions between the bone fracture surface and surrounding tissue. These adhesions may reduce or hinder the normal movement of the area of repair by restricting the natural movement of tendons over the adjacent bone. Moreover, the ingrowth of adhesions into surrounding nerve fibers may disrupt the transmission of impulses along the nerve fiber with a resultant diminution of sensory or motor function.

Various attempts to minimize the fibrous adhesions have met with only limited success. Conventional therapy involves the application of passive motion to the affected area during the healing period. If adhesion formation is severe, then a second surgical operation, tenolysis, is often required to remove the adhesions. These remedies offer only temporary relief from the deleterious effects of the adhesions, and these remedies do not prevent the formation of more adhesions subsequent to application of the relief. Therefore, a need exists for a means of inhibiting the formation of fibrous adhesions between bone fractures and the surrounding tissue during the healing process.

SUMMARY OF THE INVENTION

In accordance with the present invention, disclosed is a method of treating a bone fracture which involves interposing a barrier layer of soft biological tissue at the interface of said bone fracture and the surrounding tissue, said layer of biological tissue having overall dimensions sufficient to substantially cover the outer surface of the bone fracture and separate it from the surrounding tissue.

DETAILED DESCRIPTION OF THE INVENTION

Figure 1:
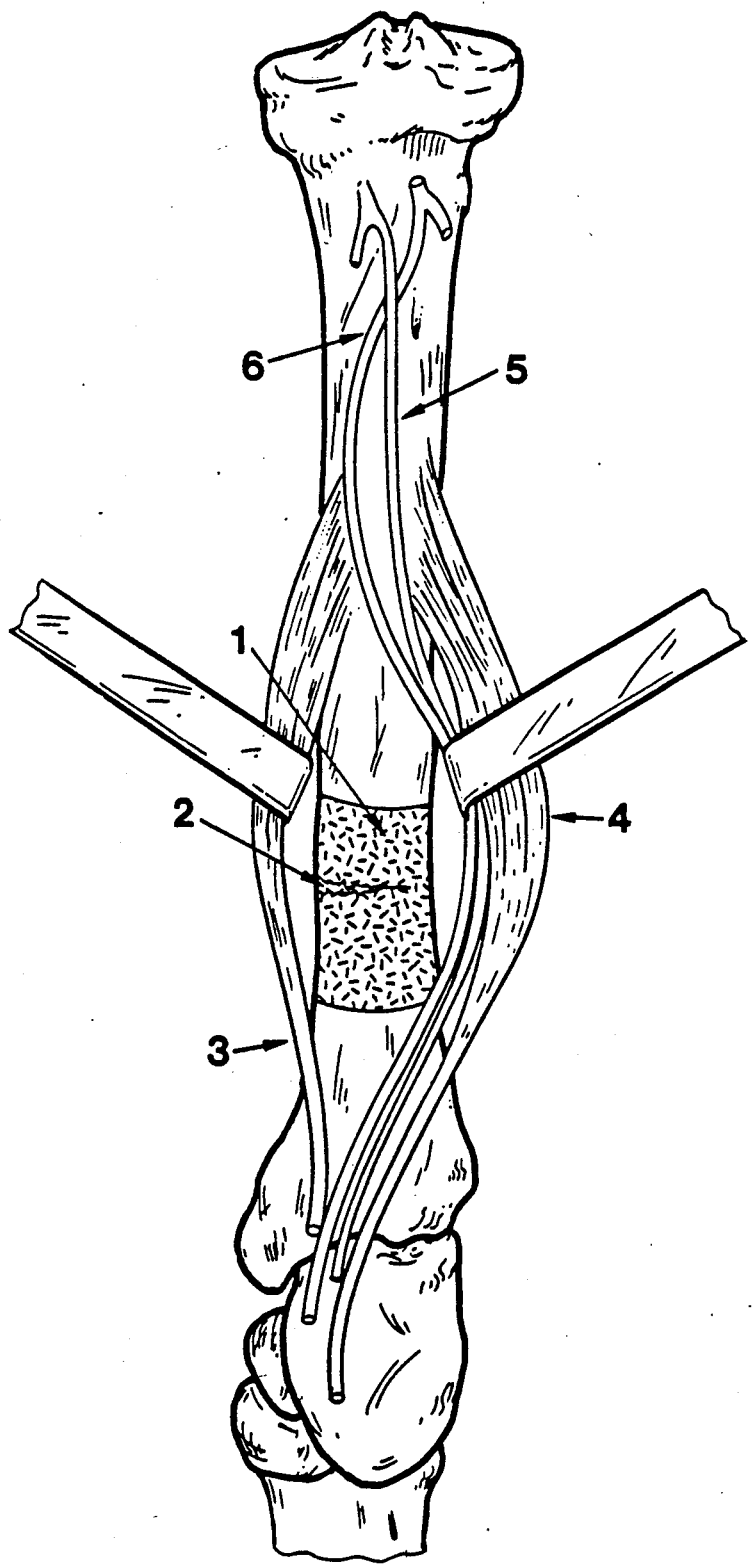
FIG. 1 is a perspective view of the posterior surface of a fractured human tibia being treated according to the method of the present invention.

In accordance with the present invention, a soft biological material is interposed between a bone fracture and the surrounding tissue. By way of example, a bone fracture may be sheathed with a piece of bioprosthetic material during surgical repair of damaged tendons or bones. The bioprosthetic tissue advantageously protects surrounding tissue from the deleterious effects caused by the irregular bone edges of the fracture, promotes free tendon and muscle gliding over the bone fracture site, and provides a suitable environment around the bone fracture to maintain the range of motion and flexibility of the repair area. Surrounding tissue includes tendons, muscles, nerves, blood vessels, and the like.

For purposes of illustrating the present invention, FIG. 1 illustrates the insertion of bioprosthetic tissue around a fractured tibia. The bioprosthetic tissue is applied to the surface of the bone to interface between the area of fracture and the surrounding tissue, forming a barrier. The bioprosthetic tissue 1 is in sheet form and is inserted between the surface of the bone fracture 2 and the surrounding tendons 3, muscle 4, nerves 5, blood vessels 6, and other surrounding tissue. The bioprosthetic tissue can be free-floating and held in place by friction with the bone and surrounding tissue. Alternatively, it may be secured to the bone by any suitable means such as cementing or attachment with surgical screws or staples.

Prior to application of the bioprosthetic material, displaced fractures are preferably set. In severe cases, bone grafting and other techniques may be employed. The bioprosthetic material not only isolates the bone fracture from surrounding tissue, thus inhibiting fibrous adhesions, but also promotes healing of the bone in a smooth, non-abrasive surface.

The shape and dimensions of the bioprosthetic tissue will vary, depending upon the length and surface area of the bone fracture. Generally, the shape is square or rectangular. In a preferred embodiment of the invention, the barrier has dimensions sufficient to cover the fracture surface, and which are sufficient to extend beyond the edge of the fracture surface a short distance as shown in FIG. 1.

The bioprosthetic tissue is made of soft biological tissue, such as naturally occuring biological tissue derived from animal sources. Suitable animal sources can include but are not limited to bovine, porcine, horse, sheep, kangaroo, or rabbit. The tissue may be obtained from various parts of the anatomy, as described below. Alternatively, the soft biological tissue can be composed of collagen or reconstituted collagen substitutes including but not limited to collagen-fabric films, collagen membranes, reconstituted collagen on Dacron ® mesh, tanned collagen sponge grafts and the like. In accordance with the present invention, the soft biological tissue barriers provide a moist, lubricious, and flexible interface between the irregular bony edges of the bone fracture and the surrounding tissue, and inhibits the formation of fibrous adhesions between the bone edges and the surrounding tissue. Moreover, the soft biological tissue is stable and nonantigenic when placed into the body.

In preparing the bioprosthetic material, naturally occurring biological tissue is removed from its host, defatted if necessary and processed by one of several well-known procedures used to prepare the tissue for implantation into humans. The tissue may be fixed (tanned) conventionally in from about 0.2 to about 0.6 weight percent glutaraldehyde in either phosphatebuffered solutions, or phosphate-free buffers as described in the copending U.S. patent application Ser. No. 445,345 filed on Nov. 29, 1982. The tissue handling conditions, as conventionally known, are not considered part of the present invention unless otherwise stated. Likewise, tissue may be sterilized conventionally, using radiation or exposure to ethylene oxide, or by immersion in about 0.625 percent glutaraldehyde or from about 4 to about 5 percent formaldehyde. A particularly preferred sterilant is a combination of about 4 weight percent formaldehyde, about 22 weight percent ethanol and about 1.2 weight percent of a surfactant such as polysorbate 80.

Naturally occurring biological tissue in accordance with the present invention includes, but is not limited to, epithelial and fibrous connective tissue such as pericardial tissue, *dura mater, fascia lata,* amnion, tendon, ligament, cartilage, and the like. The epithelial tissues such as *dura mater,* amnion, *facia lata,* and pericardium generally comprise two layers each; a fibrous, proteinaceous layer and a relatively smooth membranous layer. In accordance with a preferred embodiment of the present invention, the rough, fibrous layer of the tissue is placed against the bone to provide better anchoring to the bone surface, while the smooth, membranous layer is directed toward the surrounding tissue and provides a more lubricious surface. In accordance with the preferred embodiment of the present invention, pericardial tissue which has been tanned with glutaraldehyde is employed as the interpositional bioprosthetic material.

In accordance with a preferred embodiment of the present invention, the natural biological tissue is treated prior to implantation to render it substantially resistant to calcification. This treatment advantageously maintains the biological tissue in a more flexible state than calcified tissue, allowing the tissue to conform better to the uneven surface of the bone, and provides a softer surface to prompt better bone healing. Calcification mitigation treatments of biological tissue are not considered part of the present invention but can be found in copending U.S. patent applications Ser. Nos. 445,345 filed Nov. 29, 1982; 377,747 filed May 13, 1982; now U.S. Pat. No. 4,481,009 and 441,023 filed Nov. 12, 1982; and in U.S. Pat. No. 4,323, 358.

EXAMPLE

The following test demonstrates a significant reduction in fibrous adhesions between a bone fracture of a rabbit tibia and the surrounding tissues when using biologically inert material as a barrier between the bone and the surrounding tissue as compared to a control model. A trauma simulating a fracture was imparted to the tibia bone proximal to the tibia-ankle joint of a rabbit. A piece of glutaraldehyde-processed bovine pericardium having a shape and size sufficient to cover the fracture was applied to the surface of the bone fracture.

Bone fractures prepared as above in a control group of rabbits were not sheathed with any bioprosthetic tissue. A 62% reduction in visually-observed fibrous adhesions on resected bone when using the bioprosthetic tissue was noted. In addition, free tendon gliding over the subjacent bone fracture was observed in the experimental group, whereas minimal free tendon gliding was observed in the control group. Thus, the bioprosthetic tissue inhibited the formation of fibrous adhesions and increased the post-operative range of motion of the repair area.

The present invention has been described in detail and with specific reference to its preferred embodiments; however, it will be understood by those skilled in the art that modifications can be made thereto without departing from the spirit and scope thereof.

What is claimed is:

1. A method of treating a bone fracture to substantially inhibit the formation of fibrous adhesions between the bone fracture surface and the surrounding tissue during the healing process, which comprises interposing a barrier layer of soft bioprosthetic tissue at the interface of said bone fracture and the surrounding tissue.

2. The method of claim 1 wherein said bioprosthetic tissue is naturally occurring biological tissue which is fixed with a tanning agent prior to being interposed as said barrier layer.

3. The method of claim 2 wherein the biological tissue is selected from epithelial or fibrous connective tissue.

4. The method of claim 2 wherein the biological tissue is selected from the group consisting of pericardial tissue, *dura mater, fascia lata,* and amnion.

5. The method of claim 4, wherein the biological tissue is derived from a source selected from the group consisting of bovine, porcine, horse, sheep, kangaroo and rabbit sources.

6. The method of claim 2 wherein the biological tissue is treated prior to implantation to render it substantially resistant to calcification.

7. The method of claim 6 wherein the biological tissue is pericardial tissue.

8. The method of claim 2 wherein the tanning agent is glutaraldehyde.

9. The method of claim 1 wherein the overall dimensions of said barrier layer are sufficient to substantially cover the outer surface of said bone fracture.

* * * * *